US008875589B1

(12) United States Patent
Mancinho et al.

(10) Patent No.: US 8,875,589 B1
(45) Date of Patent: Nov. 4, 2014

(54) SAMPLING AND COUNTING SYSTEM

(75) Inventors: Derek J. Mancinho, Laramie, WY (US); Myat S. Win, Nottingham, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 302 days.

(21) Appl. No.: 13/474,205

(22) Filed: May 17, 2012

(51) Int. Cl.
*G01N 1/26* (2006.01)

(52) U.S. Cl.
USPC ............... 73/863.03; 73/863.33; 73/31.07

(58) Field of Classification Search
CPC .................................................. G01N 1/2247
See application file for complete search history.

(56) References Cited

U.S. PATENT DOCUMENTS

| | | | | |
|---|---|---|---|---|
| 4,246,788 A | * | 1/1981 | Olin et al. ................. | 73/863.03 |
| 7,667,839 B2 | * | 2/2010 | Bates ........................... | 356/337 |
| 2009/0178494 A1 | * | 7/2009 | Liu et al. .................... | 73/863.31 |
| 2011/0044853 A1 | * | 2/2011 | Devine ........................ | 422/33 |

* cited by examiner

*Primary Examiner* — Paul West
(74) *Attorney, Agent, or Firm* — Ulysses John Biffoni

(57) ABSTRACT

A system for testing the efficiency of a test HEPA filter, the system comprises a dilution system and a sampling system. The dilution system processes samples collected upstream of the test HEPA filter. The dilution system has a test portion and a calibrated portion. The calibrated portion aids in determining the dilution ratio of the test portion thereby rendering the dilution system self-calibrating. The sampling system receives upstream samples via the dilution system, and downstream samples collected directly downstream of the test HEPA filter. The sampling system incorporates a flow rate balancing system to ensure accurate counts with respect to samples collected upstream and downstream of the test HEPA filter. The sampling system works well with particle counters fitted with relatively weak fans to draw in samples for counting; this is achieved by connecting the sampling system to both the inlet and exhaust outlet of a particle counter.

16 Claims, 7 Drawing Sheets

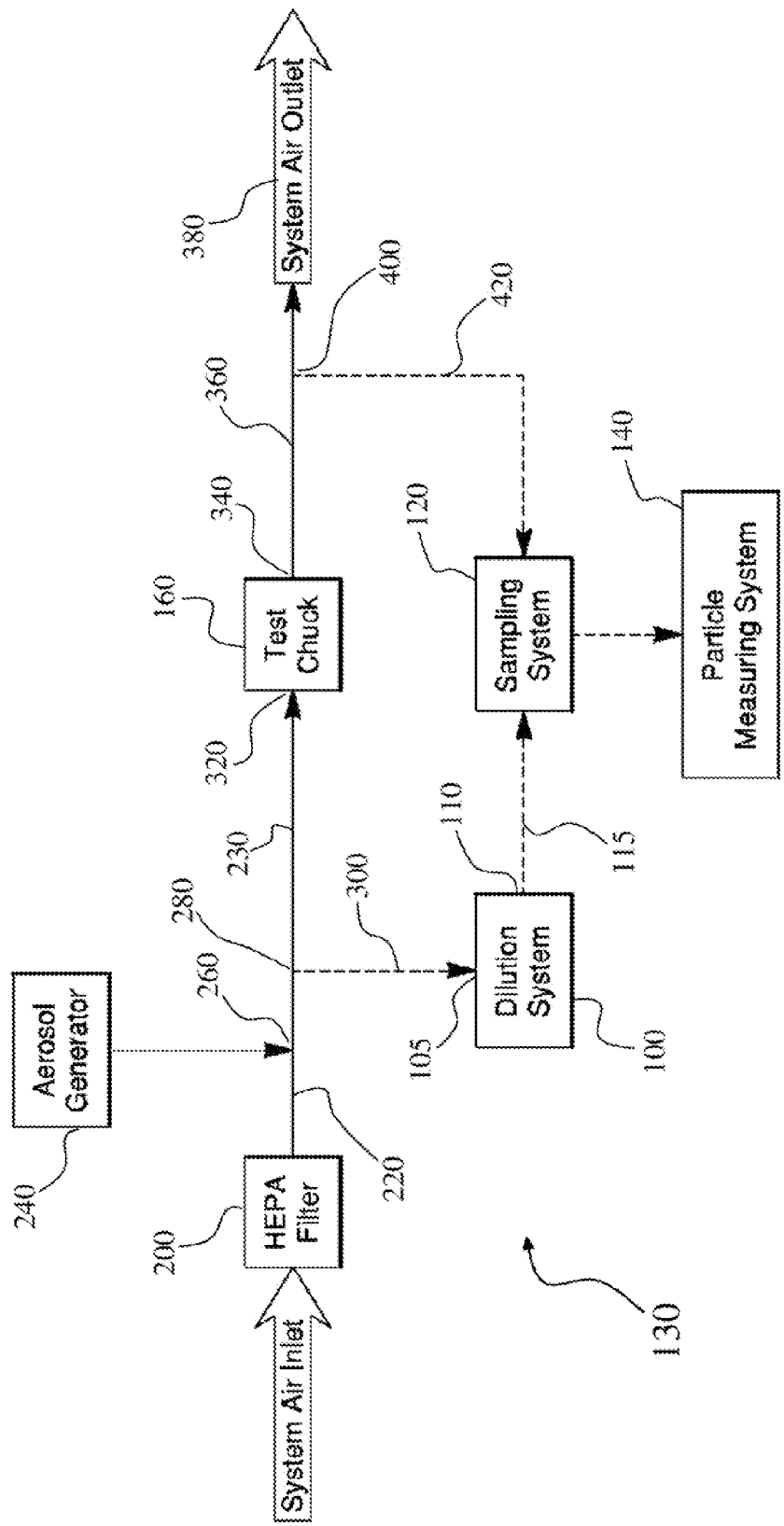

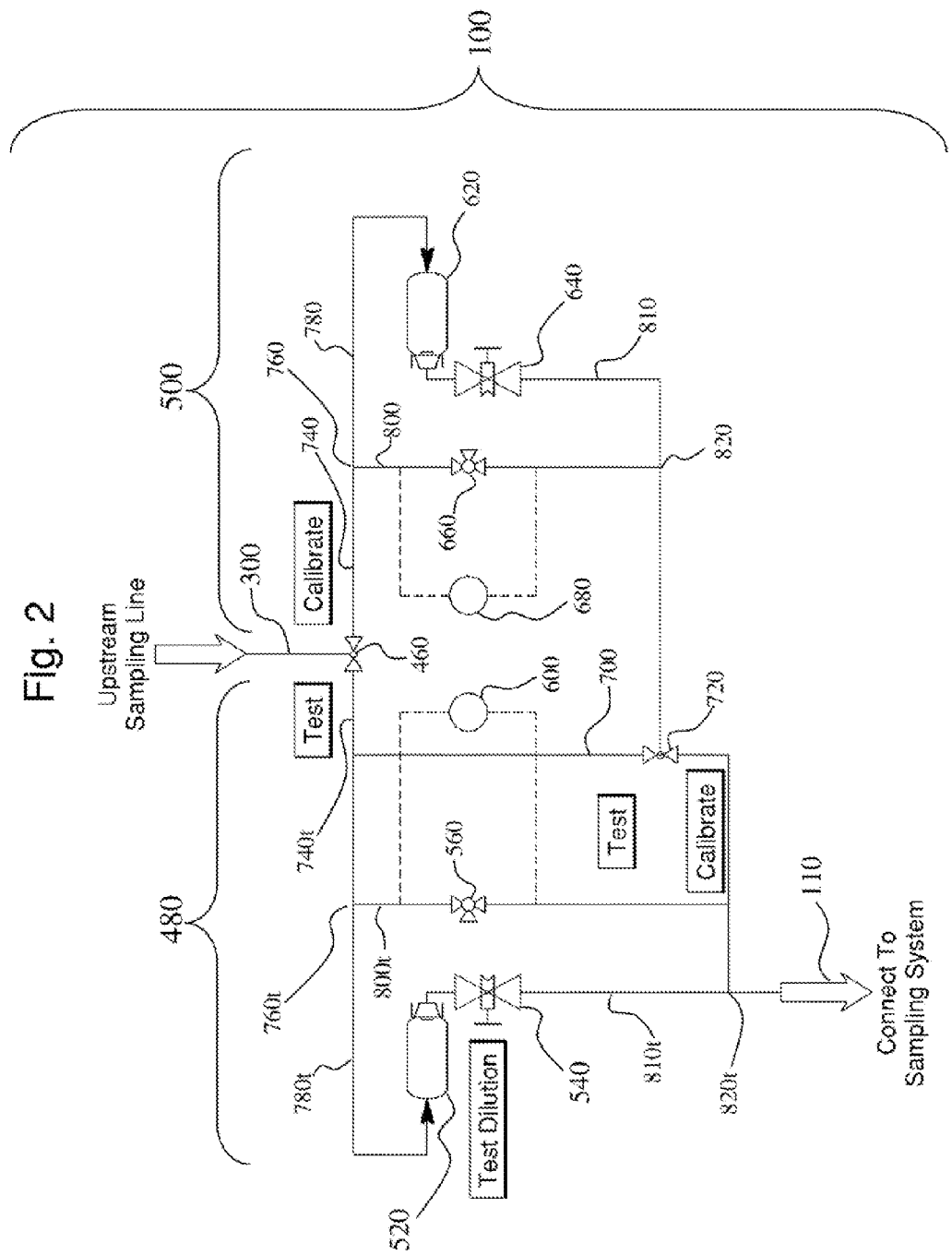

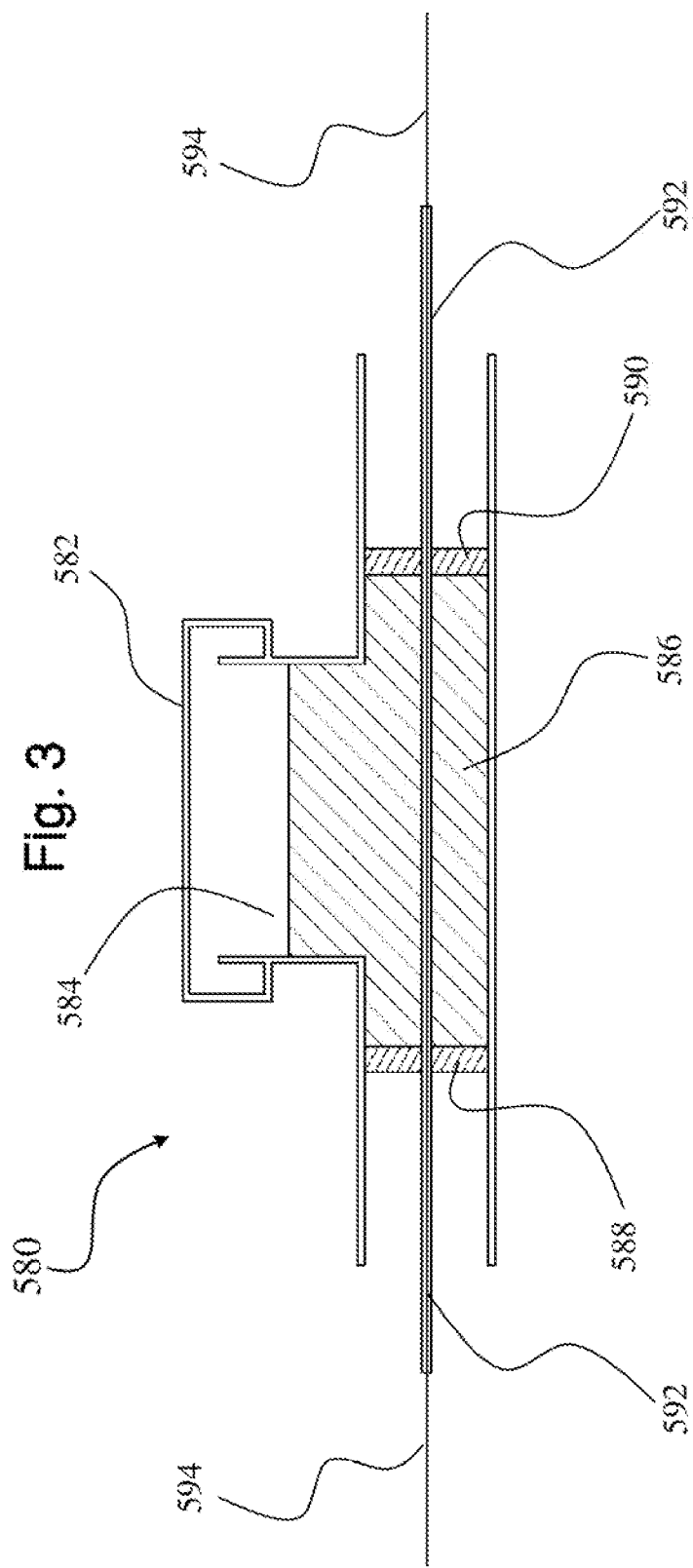

TABLE 1

For a Particle Measuring System 140 rated at 1cf/min (60cf/hr) sample rate

| Particle measuring system 140 status | Upstream Rotameter 1160 Flow rate (cf/hr) | Downstream Rotameter 1100 Flow rate (cf/hr) | 3-way Sample Control Valve 940 and 3-Way Ball valve 960 configuration |
|---|---|---|---|
| Off | 80 | 80 | Moot |
| On | 80 | 80 | No flow permitted through particle measuring system 140 |
| On | 20 | 80 | Configured to deliver upstream sample to particle measuring system 140 |
| On | 80 | 20 | Configured to deliver downstream sample to particle measuring system 140 |

Fig. 5

SAMPLING AND COUNTING SYSTEM

GOVERNMENT INTEREST

The invention described herein may be used, manufactured, and licensed by or for the United States Government.

FIELD OF THE INVENTION

This invention relates to a high flow rate self-calibrating aerosol dilution device, and a sampling system for providing particulate samples to a particle counter. The invention can be used for testing High-Efficiency Particulate Air (HEPA) filters by collecting samples up and downstream of the HEPA filter under test and comparing upstream and downstream sample counts.

BACKGROUND OF THE INVENTION

As noted in U.S. Pat. No. 7,536,898 issued to Owen, when particle counters measure aerosol concentrations above their operating range, the detectors can become saturated or exhibit undesirable nonlinear behavior. The drawback from these measurement devices arises when they are used to measure aerosol concentrations above the instrument's dynamic range.

To overcome this obstacle, dilution techniques have been employed where the aerosol concentration is diluted by separating the flow path of an aerosol into a filtered path and a non-filtered path. In the filtered path, a filter absorbs the aerosol particles to create relatively pure air which is then mixed with the unfiltered aerosol to create a diluted mix. The diluted mix is then channeled to a particle counter and the collected count data extrapolated to arrive at a particle concentration, which depends on the actual dilution factor created by the diluter. It is often difficult to determine the dilution factor accurately, leading to inaccurate and disputed counts.

The current generation of particle counters is typically designed to measure particulates in clean rooms (also known as "white rooms") and obtain statistically significant counts based on relatively high sample volumes typically of the order of cubic feet. Consequently, such counters are easily overwhelmed if exposed to high particulate counts. However, it is particularly advantageous to use such particle counters because when operating properly they provide very accurate particle counts. Therefore, a dilution and sampling system that can be used in combination with modern particle counters is highly desired.

U.S. Pat. No. 7,998,252 issued to Huza et al. describes an apparatus and method for certifying a filter in a containment system without decontaminating the containment system prior to certification. The apparatus generally comprises a valve assembly selectable between at least three operational states. A first state prevents flow through a port in housing. A second state fluidly couples the port to test equipment necessary to test a filter disposed within the housing. A third state seals the port but fluidly couples the test equipment to a decontamination system.

U.S. Pat. No. 7,785,408 issued to Jordan Sr., et al describes a particle collector made up of a housing defining an enclosed chamber. An inlet opening in the housing provides fluid communication between a source of gas and particles and the chamber and an outlet opening provides fluid communication between the chamber, and the exterior of the housing. The outlet opening is connected to a pump for drawing gas and particles through the housing from the inlet opening to the outlet opening. A collecting member having an adhesive on at least a portion of the surface is disposed in the chamber between the inlet opening and the outlet opening. The adhesive surface of the collecting member is positioned adjacent to the inlet opening. When gas and particles are drawn through the housing, the inlet opening directs a stream of gas and particles at the surface of the collecting member. Particles having an aerodynamic equivalent diameter of less than about 2.5 μm (2.5 microns) are captured.

While such technologies as described above have some merit there is a need for improved dilution and sampling apparatus to enable, for example, the testing of HEPA filters using a new generation of particulate counters that normally measure particulates in clean rooms.

SUMMARY OF THE INVENTION

A system for testing the efficiency of a test HEPA filter includes improved dilution and sampling systems. The dilution system processes samples collected upstream of the test HEPA filter. The dilution system has a test portion and a calibration portion. The calibration portion aids in determining the dilution ratio of the test portion thereby rendering the dilution system self-calibrating, and allowing an accurate particle count upstream and downstream from the test HEPA filter. The sampling system receives upstream samples via the dilution system, and downstream samples collected directly downstream of the test HEPA filter. The sampling system incorporates a flow rate balancing system to ensure accurate counts with respect to samples collected upstream and downstream of the test HEPA filter. The sampling system allows the use of a new generation of accurate static particle counters, normally fitted with relatively weak fans to draw in samples from clean rooms and the like for counting in the present dynamic HEPA filter test system. The use of such counters in the present system is achieved by connecting the sampling system to both the inlet and exhaust outlet of a particle counter.

BRIEF DESCRIPTION OF THE DRAWINGS

FIG. 1A shows a schematic diagram of a filter test system which incorporates dilution and sampling systems according to the present invention.

FIG. 2 shows a schematic of the dilution system according to the present invention.

FIG. 3 shows a cross-sectional view of a modified union-tee used in the dilution system according to the present invention.

FIG. 5 shows a Table of operation of the sampling and counting systems according to the present invention.

DETAILED DESCRIPTION OF THE INVENTION

This invention is directed to a high flow rate self-calibrating aerosol dilution device, and a sampling system for providing particulate samples to a particle counter. The invention can be used for testing High-Efficiency Particulate Air (HEPA) filters by collecting samples up and downstream of the HEPA filter under test and comparing upstream and downstream sample counts to calculate HEPA filter efficiency.

For the purposes of this invention disclosure, the terms "line" and "pathway" are regarded as equivalent terms; in addition, the terms "particle measuring system" and "particle counter" are regarded as equivalent terms.

Broadly, the invention is a system for testing the efficiency of a test HEPA filter. The testing system comprises improved dilution and sampling systems for particular use with a new generation of highly accurate static particle counters, typically used to count particles in clean rooms and the like. The dilution system is capable of test and self-calibration modes of operation to improve accuracy of particle counters. The dilution system processes samples collected upstream of the test HEPA filter. The calibrated portion aids in determining the dilution ratio of the test portion thereby rendering the dilution system self-calibrating. The sampling system receives upstream samples via the dilution system, and downstream samples collected directly downstream of the test HEPA filter. The sampling system incorporates a flow rate balancing system to ensure accurate counts with respect to samples collected upstream and downstream of the test HEPA filter. The sampling system works well with static particle counters fitted with relatively weak fans to normally draw in samples for counting. In this invention, the sampling system is connected to both the inlet and exhaust outlet of a particle counter.

Figure 1B:
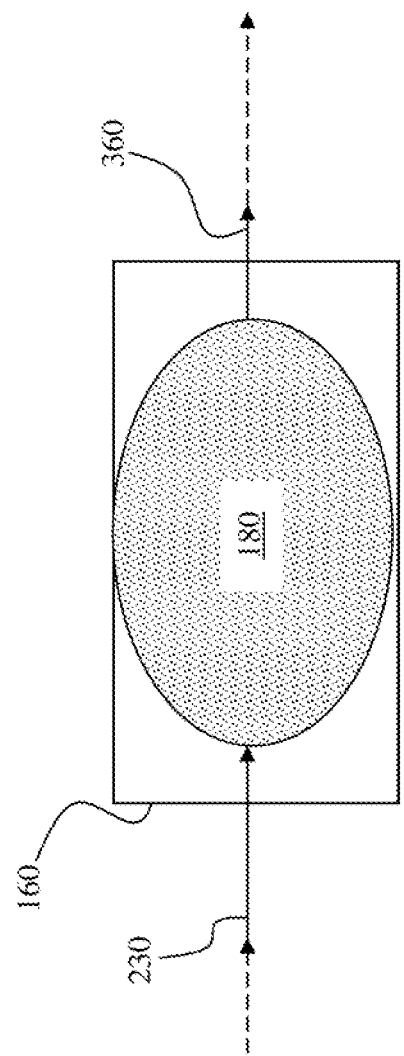
FIG. 1B shows a test chuck according to the present invention.

Referring to the Figures of which FIG. 1A shows a schematic diagram of an overall HEPA filter test system 130, which includes a dilution system 100 and sampling system 120 of this invention. The dilution system 100 has an inlet 105 and an outlet 110. In one embodiment the outlet 110 of the dilution system 100 is coupled to a sampling system 120 via pathway 115 as shown in FIG. 1A. The sampling system 120 is operatively coupled to a particle measuring system 140. The dilution system 100 and sampling system 120 respectively receive samples upstream and downstream of a test chuck 160. The test chuck 160 includes a test HEPA filter 180 under test (shown-schematically in FIG. 1B). The efficiency of the test HEPA filter 180 is determined by comparing the particulate counts upstream and downstream of the test HEPA filter 180 which may be located in a test chuck 160.

Still referring to FIG. 1A, system air is directed through a system air HEPA filter 200 where the system air is filtered of particulates if present in the system air. The filtered system air is directed along conduit pathway 220 towards test chuck 160. An aerosol generator 240 provides an aerosol, the equivalent of particulate matter, which is directed to conduit pathway 220 where the aerosol is mixed with the filtered system air at pathway junction 260 to provide a mixture of filtered system air and aerosol hereinafter referred to as undiluted aerosol. The undiluted aerosol is directed along upstream sampling line 230 to the test chuck 160 and the test HEPA filter 180 therein. The upstream sampling line 230 is located upstream of the test chuck 160 and more specifically extends between junction 260 from the aerosol generator and the test chuck 160.

As shown in FIG. 1A, at junction 280 in the upstream sampling line 230 undiluted aerosol is directed both towards test chuck 160 and along upstream sampling line 300 to the dilution system 100. The test HEPA filter 180 located in test chuck 160 filters undiluted aerosol arriving at test chuck inlet 320 and the filtered undiluted aerosol is directed from test chuck outlet 340 and thence along outlet pathway 360 to a system outlet 380. Samples of filtered undiluted aerosol are drawn off downstream of test chuck 160 at junction 400 on outlet pathway 360 and directed along pathway 420 to the sampling system 120. It should be noted that pathways 115 and 420 respectively deliver upstream and downstream samples to the sampling system 120 (see FIG. 4).

In broad terms, the dilution system 100 forms part of a HEPA filter test system 130 for testing the efficiency of a test HEPA filter 180. The dilution system 100 comprises a test portion 480 comprising a first means for diluting an upstream sample, and a calibrate portion 500 for calibrating the test portion 480, the calibrate portion 500 comprises a second means for diluting an upstream sample. The test portion 480 and calibrate portion 500 are operably linked such that during calibration of the test portion 480 an upstream sample first enters the calibrate portion 500 and from the calibrate portion the sample enters the test portion 480, and during test mode only the test portion 480 is used to dilute upstream samples.

An exemplar non-limiting embodiment of the dilution system 100 is shown in FIG. 2. Undiluted aerosol is drawn into the dilution system 100 via upstream sampling line 300. The dilution system 100 comprises a test portion 480 and a calibrate portion 500. A valve 460, such as a three-way ball valve, directs the undiluted aerosol to the test portion 480 or the calibrate portion 500 of the dilution system 100; moreover undiluted aerosol can be sent to the calibrate portion 500 and thence through the test portion 480 as explained below. The test portion 480 is generally used to obtain test data on the efficiency of the test HEPA filter 180 and the calibrate portion 500 is used to determine the dilution ratio of the test portion 480 of the dilution system 100.

The test portion 480 is essentially a parallel circuit as shown in FIG. 2, which is made up of a test portion HEPA filter 520; a first test portion restriction valve 540 which may be a needle valve; a second test portion restriction valve 560, which can be a modified union tee 580 (shown in more detail in FIG. 3); and a test portion differential pressure gauge 600 for measuring the pressure differential across the second test portion restriction valve 560. The test portion differential pressure gauge 600 can be any suitable pressure gauge such as, but not limited to, a magnehelic pressure differential gauge which is available from Dwyer Instruments, Inc. The second test portion restriction valve 560 is located parallel to the test portion HEPA filter 520 and first test portion restriction valve 540. The first test portion restriction valve 540 is in series with respect to the test portion HEPA filter 520. In FIG. 2 the first test portion restriction valve 540 is shown downstream of the test portion HEPA filter 520, but it can also be located upstream of the test portion HEPA filter 520, but downstream is preferred. While the first test portion restriction valve 540 is shown parallel to and not in series with respect to the second test portion restriction valve 560 it still follows that any adjustment to the first test portion restriction valve 540 will impact on the flow rate of undiluted aerosol through the second test portion restriction valve 560.

In test mode of the dilution system 100 undiluted aerosol is directed into the test portion 480 by adjusting valve 460 to direct output from Upstream sampling line 300 along pathway 740t where the undiluted aerosol is separated at a first test portion junction 760t into test portion filtered path 780t and a test portion unfiltered but flow restricted path 800t. The paths 780t and 800t are essentially in parallel with respect to each other. The test portion restricted path 800t includes the second test portion restriction valve 560 which in a preferred embodiment is a modified union tee 580 as shown in FIG. 3. The test portion filtered path 780t includes the test portion HEPA filter 520 and the first test portion restriction valve 540 located in series with respect to the test portion HEPA filter 520. The second test portion restriction valve 560 allows a measured amount of undiluted aerosol to bypass the test portion HEPA filter 520. The first test portion restriction valve 540 is adjusted which controls the flow through test portion HEPA filter 520 and hence also through second test portion restriction valve 560. As long as the pressure across the second test portion restriction valve 560 is kept at a selected set point a set dilution is maintained. The test portion HEPA filter 520 removes the particles in the undiluted aerosol to create pure air which is directed along test portion filtered path 810*t*. The second test portion restriction valve 560 restricts flow of undiluted aerosol and the restricted flow of undiluted aerosol from the second test portion restriction valve 560 is directed to second test portion junction 820*t* and mixed with pure air from test portion HEPA filter 520.

The test portion 480 also includes a test line 700 which in turn includes a three-way valve 720 (see FIG. 2). The three-way valve 720 can be any suitable valve such as a three-way ball valve. The three-way valve 720 can be used to direct output from the calibrate portion 500 of the dilution system 100 to the test portion 480 of the dilution system 100 via test line 700 such that during the self-calibration mode of operation undiluted aerosol is processed consecutively through the calibrate portion 500 and then the test portion 480 of dilution system 100 and thence onto sampling system 120 for particle counting.

During the self-calibration mode of operation particle counts are obtained using both portions 500 and 480 to calibrate the test portion 480 of the dilution system 100. Then particle counts made using only the test portion 480 are compared to the particle counts obtained using both portions 500 and 480 to calibrate the test portion 480 of the dilution system 100. While it is preferred that during the self-calibration mode of operation that counts are made first based on consecutive dilution using the calibrate and test portions 500 and 480, and then the test portion 480 only.

In test mode only the test portion 480 of the diluter system 100 is used to test samples upstream of the test chuck 160. Particle counts from samples collected up and downstream of the test chuck 160 are compared to determine the efficiency of the HEPA filter 180 in test chuck 160. The upstream samples are processed by the test portion 480 of the dilution system 100. The downstream samples are processed directly by the sampling system 120 (see FIG. 4).

In one embodiment the first means for diluting an upstream sample comprises test portion HEPA filter 520, first test portion restriction valve 540, and second test portion restriction valve 560, first test portion junction 760*t*, test portion filtered path 780*t*, test portion restricted path 800*t*, test portion filtered path 810*t*, and second test portion junction 820*t*. However, it should be understood that the first means for diluting an upstream sample can include any apparatus that provides the same functionality as the test portion 480. The second means for diluting a downstream sample comprises calibrate portion HEPA filter 620, first calibrate portion restriction valve 640, and second calibrate portion restriction valve 660, first calibrate portion junction 760, calibrate portion filtered path 780, calibrate portion restricted path 800, calibrate portion filtered path 810, and second calibrate portion junction 820. However, it should be understood that the second means for diluting an upstream sample can include any apparatus that provides the same functionality as the calibrate portion 500.

Referring to FIG. 3, the modified union tee 580 comprises a closed top 582, and an interior 584 at least partly filled with epoxy resin 586 with optional first and second gaskets 588 and 590 located proximate to opposite ends of the modified union tee 580. A steel tubing 592 passes through the epoxy resin 586 and inside the steel tubing 592 is a wire 594. The wire 594 can be made out of stainless steel serves to restrict unfiltered aerosol flow through the steel tubing 592 and hence through the modified union tee 580. The diameters of the steel tubing 592 and wire 594 therein are selected to achieve a desired degree of restriction and particle flow through the modified union tee 580. The amount and distribution of epoxy resin 586 inside interior 584 (and hence inside the modified union tee 580) is sufficient to ensure the flow of unfiltered aerosol is limited to flow through the steel tubing 592. The gauge of the wire 594 is selected to further limit the flow of unfiltered aerosol through the steel tubing 592 and hence through the modified union tee 580.

By comparing the counts from using both portions 500 and 480 with the count from using only test portion 480 enables an operator to determine the dilution ratio of the test portion 480 of the dilution system 100; in effect, the calibrate portion 500 calibrates the test portion 480. Subsequent counts performed using just the test portion 480 in combination with the sampling system 120 and particle measuring system 140 enable an operator to determine the particle count upstream of the test chuck 160. In normal sample test mode only the test portion 480 is in use; specifically, the calibrate portion 500 is used to calibrate the test portion 480 of the dilution system 100 thus making the dilution system 100 a self-calibrating dilution system.

The calibrate portion 500 is made up of a calibrate portion HEPA filter 620; a first calibrate portion restriction valve 640 which may be a needle valve; a second calibrate portion restriction valve 660, which can be a modified union tee 580 (shown in more detail in FIG. 3); and a calibrate portion differential pressure gauge 680 for measuring the pressure differential across the second calibrate portion restriction valve 660. The calibrate portion differential pressure gauge 680 can be any suitable pressure gauge such as but limited to, a magnehelic pressure differential gauge which is available from Dwyer Instruments, Inc. The second calibrate portion restriction valve 660 is located parallel to the calibrate portion HEPA filter 620 and the first calibrate portion restriction valve 640. The first calibrate portion restriction valve 640 is in series with respect to the calibrate portion HEPA filter 620. In FIG. 2 the first calibrate portion restriction valve 640 is shown downstream of the calibrate portion HEPA filter 620, but it can also be located upstream of the calibrate portion HEPA filter 620, but downstream is preferred. While the first calibrate portion restriction valve 640 is shown parallel to and not in series with respect to the second calibrate portion restriction valve 660 it still follows that any adjustment to the first calibrate portion restriction valve 640 will impact on the flow rate of undiluted aerosol through the second calibrate portion restriction valve 660.

The dilution system 100 is a self calibrating particulate dilution system. The dilution system comprises a test portion 480 and a calibrate portion 500. The calibrate portion 500 is used to lower the concentration of particulate of undiluted aerosol received from upstream sampling line 230 via upstream sampling line 300 (see FIG. 1A).

To calibrate the dilution system 100, a sample of the undiluted aerosol is drawn through both the calibrate portion 500 and the test portion 480. This is achieved adjusting valve 460 to direct undiluted aerosol to and through the calibrate portion 500 and thence into and through the test portion 480 via valve 720 and test line 700. Once the undiluted aerosol is processed by both the calibrate portion and the test portion a count is made by the sampling system 120 in conjunction with the particle measuring system 140. Then the flow within the dilution system 100 is changed by adjusting valve 460 to direct the undiluted aerosol to only the test portion 480 and a further count is made to provide a dilution ratio of the test portion 480 for each particle size counted by the sampling system 120 in conjunction with the particle measuring system 140 and thereby calibrate the test portion 480 of the dilution system 100. Following calibration of the test portion 480 the test portion 480 is used to supply upstream samples to the sampling system 120 and the particle measuring system 140. The particle measuring system 140 can be any suitable particle counter such as a Lasair® II model 110 particle measuring system, the current version of which is a 1.0 cf/m (cubic feet/minute, equivalent to 60 cf/hr) particle counter with the ability to count particles as small as 0.1 µm.

In more detail, as shown in FIG. 2, undiluted aerosol is directed into the calibrate portion 500 by adjusting valve 460 to direct output from upstream sampling line 300 along pathway 740 where the undiluted aerosol is separated at a first calibrate portion junction 760 into calibrate portion filtered path 780 and a calibrated portion unfiltered but flow restricted path 800. The paths 780 and 800 are essentially in parallel with respect to each other. The calibrated portion restricted path 800 includes the second calibrate portion restriction valve 660 which in a preferred embodiment is a modified union tee 580 as shown in FIG. 3. The calibrate portion filtered path 780 includes the calibrate portion HEPA filter 620 and the first calibrate portion restriction valve 640 located in series with respect to the calibrate portion HEPA filter 620. The second calibrate portion restriction valve 660 allows a measured amount of undiluted aerosol to bypass the calibrate portion HEPA filter 620. The first calibrate portion restriction valve 640 is adjusted to control the flow through calibrate portion HEPA filter 620 and hence also through second calibrate portion restriction valve 660. As long as the pressure across the second calibrate portion restriction valve 660 is kept at a selected set point a set dilution is maintained. The calibrate portion HEPA filter 620 removes the particles in the undiluted aerosol to create pure air which is directed along calibrated portion filtered path 810. The second calibrate portion restriction valve 660 restricts flow of undiluted aerosol and the restricted flow of undiluted aerosol from the second calibrate portion restriction valve 660 is directed to second calibrate portion junction 820 and mixed with pure air from calibrate portion HEPA filter 620.

In test mode the sampling system 120 of the invention processes samples collected upstream and downstream of the HEPA filter 180, which can be held in a test chuck 160. The sampling system 120 works in conjunction with a particle measuring system 140. Upstream and downstream samples are respectively received via pathway conduit pathways 115 and 420 and are separately directed to the particle measuring system 140. Ina preferred embodiment the sampling system 120 is a high flow sampling system with pressure balancing; more specifically, in combination with the particle measuring system 140, the sampling system 120 ensures particle counts of upstream and downstream samples are performed under essentially the same pressure conditions to ensure accurate and meaningful particle counts.

Figure 4:
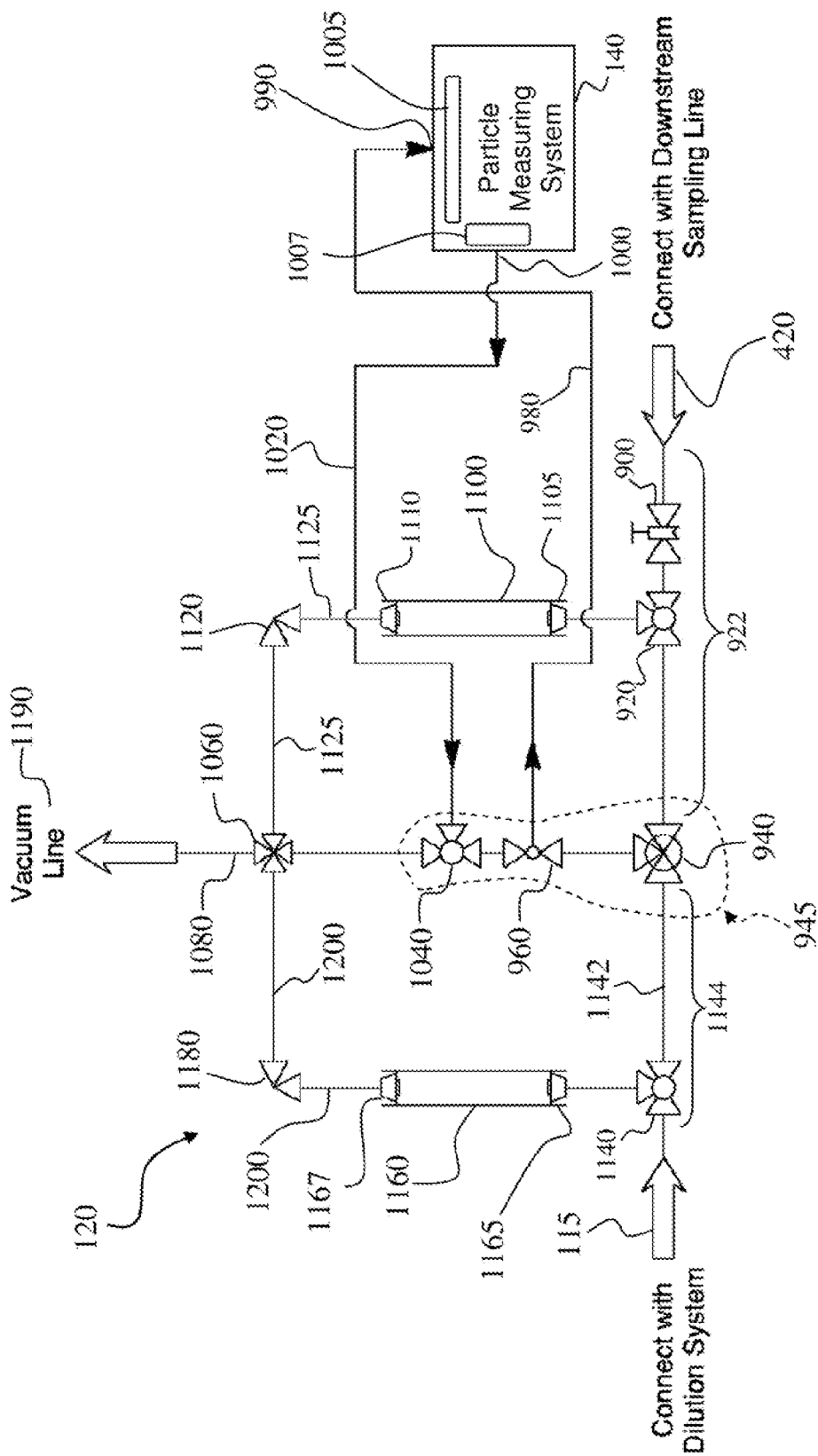
FIG. 4 shows a schematic of the sampling system coupled to a particle measuring system according to the present invention.

The particle measuring system 140 defines a sample inlet 990 and an exhaust outlet 1000 (FIG. 4); the particle measuring system 140 typically includes an internal sampling fan 1005 (shown schematically in FIG. 4). Such fans are typically relatively weak because they are used to draw in air samples for particulate counts in clean rooms (sometimes referred to as white rooms) and thus do not work against, for example, a vacuum. The present invention solves this problem by connecting the sampling system 120 to both the sample inlet 990 and also to the exhaust outlet 1000 of the particle measuring system 140.

Referring to the sampling system 120 shown in FIG. 4 and using the downstream sampling line 420 as a reference point, the downstream samples arrives via line 420 and negotiates a downstream sample line restrictor valve 900 which acts as a sample flow balance valve and may take the form of an adjustable needle valve, a downstream sample line union tee 920, a three way valve 940, and a three way ball valve 960 which is used to direct the downstream sample to the particle measuring system 140 via pathway 980 leading to the inlet 990 of the particle measuring system 140. The parts 900 and 920 are in series and collectively define the downstream sample receiving line 922 of sampling system 120. The three way valve 940 switches the sampling system 120 between upstream samples received via line 115 and downstream samples received via line 420. In this sense the three way valve 940 is a sample selector valve allowing the sampler system 120 to switch between counting upstream and downstream samples with respect to test HEPA filter 180.

A count is made by the particle measuring system 140 and the downstream sample exits the particle measuring system 140 at its exhaust outlet 1000 and is directed along exhaust outlet pathway 1020 to a union tee 1040 and thence through a union cross 1060 to a sample system exit line 1080 connected to a vacuum line 1190. The parts 940, 960 and 1040 are in series and collectively define the sample control section 945 of sampling system 120 (see FIG. 4). The downstream sample line restrictor valve 900 acts as a balance valve ensuring that the flow rate of the downstream sampling line 420 is the same as the flow rate of upstream samples through line 115 from diluter system 100 thereby balancing the flow rate through the rotameters 1100 and 1160 and the particle counter 140; this balancing is best achieved when the particle counter 140 is either switched off or otherwise isolated from the sample system 120 (it should be noted that the terms "particle measuring system" and "particle counter" are regarded as equivalent terms).

A downstream coupled rotameter 1100 is located between the union tee 920 and line 1125. The downstream rotameter 1100 defines opposite base and top ends 1105 and 1110, respectively. More specifically, the base 1105 of the downstream rotameter 1100 is attached to union tee 920 and the top of the downstream rotameter 1100 is attached to line 1125. Line 1125 includes an elbow joint 1120. The downstream rotameter 1100 measures flow rate between the downstream union tee 920 and line 1125. More specifically, the base 1105 of the downstream rotameter 1100 is attached to a downstream union tee 920 and the top 1110 of the upstream rotameter 1100 is attached to line 1125 which connects to a union cross 1060 and thence to vacuum line 1190 via sample exit line 1080. Thus, the downstream rotameter 1100 is operably linked to vacuum line 1190. The downstream rotameter 1100 measures flow rate between the downstream union tee 920 and line 1125 and hence between the downstream union tee 920 and vacuum line 1190. During upstream counts the three way ball valve 960 is used to direct the upstream sample to the particle measuring system 140 via pathway 980.

The sampling system 120 further comprises an upstream union tee 1140 and an upstream coupled rotameter 1160 associated with upstream samples received via line 115. The upstream union tee 1140 is operably coupled to the three way valve 940 via line 1142. The upstream union tee 1140 and line 1142 collectively define an upstream sample receiving line 1144 of sampling system 120. The upstream rotameter 1160 defines opposite base and top ends 1165 and 1167, respectively. The upstream rotameter 1160 is located between the union tee 1140 of upstream sample receiving line 1144 and line 1200. Line 1200 includes an elbow joint 1180. More specifically, the base 1165 of the upstream rotameter 1180 is attached to an upstream union tee 1140 and the top 1167 of the upstream rotameter 1160 is attached to line 1200 which connects to a union cross 1060 and thence vacuum line 1190 via sample exit line 1080. Thus, the upstream rotameter 1160 is operably linked to vacuum line 1190. The upstream rotameter 1160 measures flow rate between the upstream union tee 1140 and line 1200 and hence between the upstream union tee 1140 and vacuum line 1190.

The flow rate across the downstream rotameter 1100 can be adjusted by, for example, adjusting the downstream sample line restrictor valve 900 to ensure that the flow rate across the downstream rotameter 1100 is balanced and equal to the flow rate across the upstream rotameter 1160 to ensure meaningful readings of the downstream samples and diluted aerosol samples, respectively, received via pathways 115 and 420 by the particle measuring system 140.

In more detail, the sampling system 120 draws upstream and downstream air samples respectively from lines 115 and 420. More specifically, the three way valve 940 functions as a sample selector valve directing upstream or downstream samples to valve 960 and thence onto the particle measuring system 140. Prior to actual sampling the sample system 120 is balanced to provide equal flow rates with respect to both upstream and downstream samples, this is objectively achieved by balancing the flow rates through the upstream and downstream coupled rotameters 1110 and 1160 using, for example, line restrictor valve 900 which acts as a sample flow balance valve and may take the form of an adjustable needle valve. The balancing adjustment with respect to the flow rates through the up and downstream rotameters 1100 and 1160 can be performed when the particle measuring system 140 is switched off or when there is no flow of upstream or downstream samples to the particle measuring system 140. The vacuum line 1190 is also adjusted to ensure the vacuum applied to both the upstream and downstream sample lines are sufficient to achieve a flow rate through each rotameter 1100 and 1160 at about 5% to 60% higher than the flow rate of the particle measuring system 140.

In one aspect of the invention, the flow ratings of the upstream and downstream rotameters 1100 and 1160 are 5% to 60% higher than the flow rating of the particle measuring system 140. In another aspect of the invention the flow ratings of the upstream and downstream rotameters 1100 and 1160 are between 10% and 50% higher than the flow rating of the particle measuring system 140. In another aspect of the invention the flow, ratings of rotameters 1100 and 1160 are between 10% and 50% higher than the flow rate of the particle measuring system 140. In another aspect of the invention the flow ratings of rotameters 1100 and 1160 are between 15% and 30% higher than the flow rate of the particle measuring system 140. In another aspect of the invention the flow ratings of rotameters 1100 and 1160 are 25% higher than the flow rate of the particle measuring system 140.

The flow rates through the up and downstream rotameters 1100 and 1160 are a function of the strength of the vacuum applied by vacuum line 1190. Balancing (i.e., equilibrating) the flow rate through up and downstream coupled rotameters 1100 and 1160 is achieved using valve 900. More specifically, the flow rate leading from line 115 is set by the dilution system 100 thus the valve 900 is used to adjust the flow rate from line 420 associated with the downstream sample path to equal that from line 115.

For a particle measuring system 140 factory rated at 60 cf/hr (60 cubic feet per hour) the flow rate through each of the up and downstream rotameters 1100 and 1160 are set to range between 66 and 90 cf/hr with 80 cf/hr preferred with respect to each rotameter (i.e., in this non-limiting example 25% above the flow rate of a particle measuring system 140 with a 60 cf/hr rating). Table 1 in FIG. 5 shows a working example of how the flow rates through the up and downstream rotameters 1100 and 1160 may vary with respect to a particle measuring system 140 rated at 1 cubic foot volume per minute sample rate and a flow rate through the rotameters set at 25% above the flow rate of the particle measuring system 140 in this instance factory set at 1 cf/min (equating to 60 cf/hr). It should be understood that the flow rating of the particle measuring system 140 can vary according to the manufacturers specifications, but current particle measuring systems are typically rated at 1 cf/min (one cubic foot per minute sampling rate).

Another feature of the sampling system 120 is that it works well with particle counters with relatively weak internal sampling fans. This is achieved by connecting the sampling system 120 to both the sample inlet 990 and also to the exhaust outlet 1000 of the particle measuring system 140. By connecting to the inlet 990 and exhaust 1000 the internal fan 1005 of the particle measuring system 140 is not required to work against the vacuum generated by the vacuum line 1190. This novel setup enables the sampling system 120 to work in conjunction with particle counters with weak internal fans.

Figure 4A:
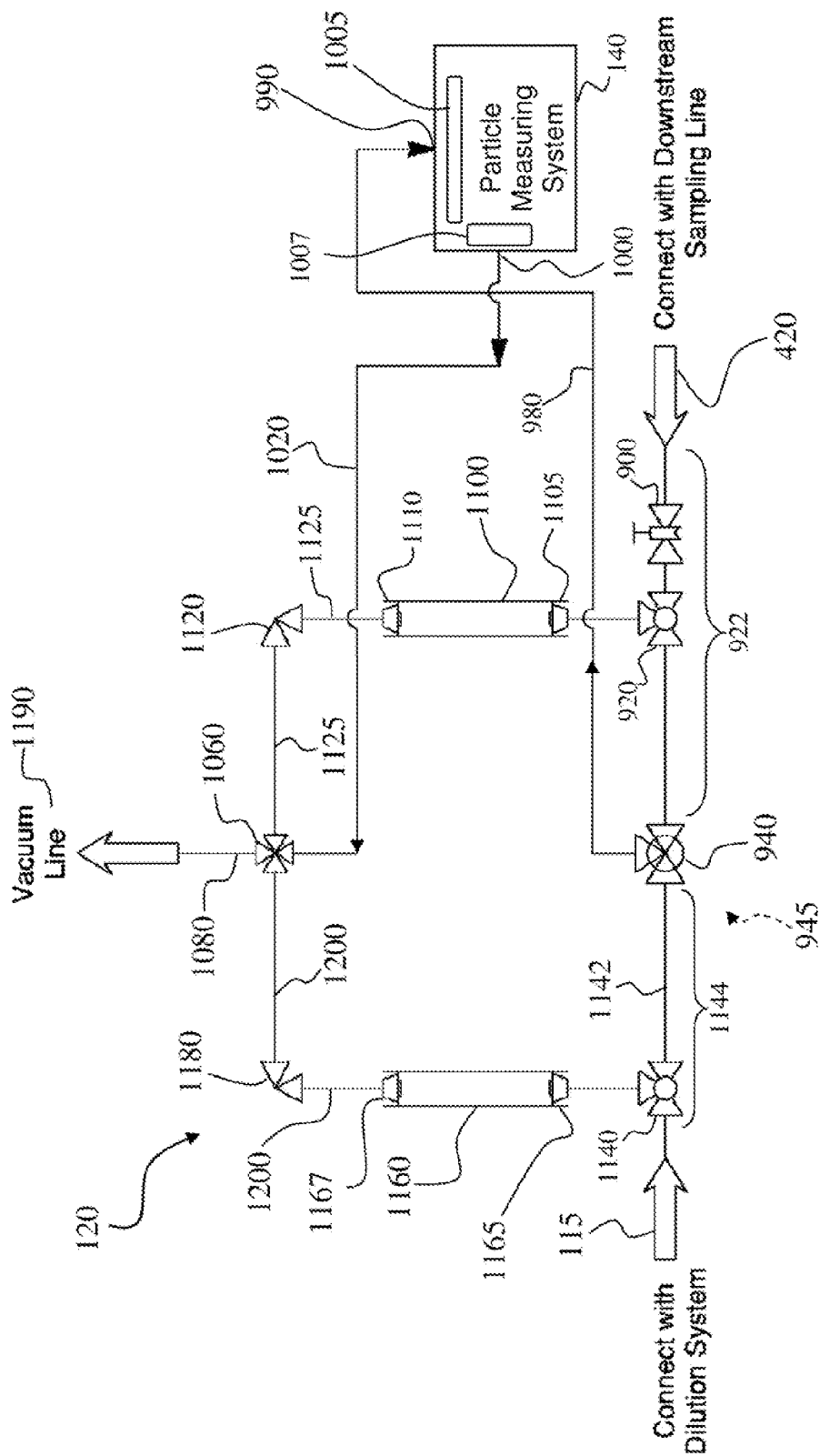
FIG. 4A shows a schematic of the sampling system coupled to a particle measuring system according to the present invention.

Referring to FIG. 4A, it will be understood by a person of ordinary skill in the art that sampling system 120 can function without valve 960 so long as pathway 980 is connected to valve 940 or its functional equivalent. However, when valve 960 is used and when valve 960 is switched such that the particle measuring system 140 is isolated and drawing sample from union tee 1040 the particle measuring system 140 will be drawing sample from its own exhaust. Because the particle measuring system 140 is designed for clean room use its exhaust is filtered by an internal ultra high efficiency particulate filter 1007 (also shown in FIG. 4) before exhausting through outlet 1000. When switched into this mode of operation the particle measuring system 140 will zero out and report no counts for any or all particle sizes. The ability to achieve a zero readout on the particulate measuring system 140 assures proper operation of the unit 140 and that no leaks are in pathway 980 or its connections at 990 and valve 960. Also, sampling system 120 can function without union tee 1040 so long as pathway 1020 is connected to union cross 1060 or a functional equivalent part.

The invention being thus described, it will be evident that the same may be varied in many ways by a routineer in the applicable arts. Such variations are not to be regarded as a departure from the spirit and scope of the invention and all such modifications are intended to be included within the scope of the claims.

What is claimed is:

1. A sampling and counting system for use in testing the efficiency of a HEPA filter by comparing particle counts of upstream and downstream samples with respect to the HEPA filter under test, the sampling and counting system comprising:
   a particle counter, the particle counter having an inlet and an exhaust outlet, the particle counter having a sample flow rating; and
   a sampling system for processing upstream and downstream samples,
       wherein the sampling system is connected to both the inlet and exhaust outlet of the particle counter, and
       wherein the sampling system incorporates a means for balancing fluid flow rate of upstream and downstream samples through the particle counter; and
   an upstream rotameter, the upstream rotameter being located between an upstream sample receiving line and a vacuum line, the upstream rotameter having an upstream rotameter flow rate, and a downstream rotameter, the downstream rotameter being located between a downstream sample receiving line and the vacuum line, the downstream rotameter having a downstream rotameter flow rate, and wherein each of the upstream and downstream rotameter flow rates are between 5% and 60% above the sample flow rating of the particle collector.

2. The sampling counting system of claim 1, wherein said particle counter is a static counter having a fan to draw in ambient air.

3. The sampling and counting system according to claim 1, wherein the means for balancing fluid flow rate of upstream and downstream samples through the particle counter is achieved at least in part by a downstream sample line restrictor valve to control the input of downstream sample flow rate into the sampling system such that the downstream sample flow rate into the sampling system equals the upstream sample flow rate into the sampling system when the particle counter is switched off or otherwise isolated from the sampling system.

4. The sampling and counting system according to claim 1, wherein each of the upstream and downstream rotameter flow rates are between 10% and 50% above the sample flow rating of the particle collector.

5. The sampling and counting system according to claim 1, wherein each of the upstream and downstream rotameter flow rates are between 15% and 30% above the sample flow rating of the particle collector.

6. The sampling and counting system according to claim 1, wherein each of the upstream and downstream rotameter flow rates are 25% above the sample flow rating of the particle collector.

7. A sampling and counting system for use in testing the efficiency of a HEPA filter, comprising:
an upstream sample receiving line;
a downstream sample receiving line;
a sample control section, wherein each of the upstream sample receiving line, the downstream receiving line and the sample control section are all operably coupled to a vacuum line;
an upstream rotameter, the upstream rotameter being located between the upstream sample receiving line and the vacuum line, the upstream rotameter having an upstream rotameter flow rating;
a downstream rotameter, the downstream rotameter being located between the downstream sample receiving line and the vacuum line, the downstream rotameter having a downstream rotameter flow rating; and
a particle counter having an inlet and exhaust outlet, the particle counter being parallel to and operably coupled to the sample control section such that both the inlet and exhaust of the particle counter are operatively connected to the sample control section, the particle counter having a sample flow rating,
wherein the sample control section includes a valve operably connected to the upstream and downstream sample receiving lines and wherein the valve in the sample control section can switch between the upstream and downstream sample receiving lines, and
wherein the downstream sample receiving line includes a downstream sample line restrictor valve for balancing the flow rate through the downstream rotameter with the flow rate through the upstream rotameter; and wherein each of the upstream and downstream rotameter flow ratings are between 5% and 60% above the sample flow rating of the particle collector.

8. The sampling counting system of claim 7, wherein said particle counter is a static counter having a fan to draw in ambient air.

9. The sampling and counting system according to claim 7, wherein each of the upstream and downstream rotameter flow ratings are between 10% and 50% above the sample flow rating of the particle collector.

10. The sampling and counting system according to claim 7, wherein each of the upstream and downstream rotameter flow ratings are between 15% and 30% above the sample flow rating of the particle collector.

11. The sampling and counting system according to claim 7, wherein each of the upstream and downstream rotameter flow ratings are 25% above the sample flow rating of the particle collector.

12. The sampling and counting system according to claim 7, further comprising a union cross, wherein the union cross is located upstream of the vacuum line, and wherein the union cross directs output flows to the vacuum from the upstream rotameter, the downstream rotameter and the exhaust outlet of the particle counter.

13. The sampling and counting system according to claim 8, wherein the particle counter has a flow rating of 60 cf/hr.

14. The sampling and counting system according to claim 7, wherein the downstream sample line restrictor valve is a needle valve.

15. A sampling and counting system for use in testing the efficiency of a HEPA filter, comprising:
an upstream sample receiving line;
a downstream sample receiving line;
a vacuum line;
an upstream rotameter, the upstream rotameter being located between the upstream sample receiving line and the vacuum line, the upstream rotameter having an upstream rotameter flow rating;
a downstream rotameter, the downstream rotameter being located between the downstream sample receiving line and the vacuum line, the downstream rotameter having a downstream rotameter flow rating; and
a particle counter having an inlet and exhaust outlet, the particle counter having a sample flow rating, wherein the exhaust outlet of the particle counter is operatively connected to the vacuum line, and the particle counter inlet is operatively connected to a valve which can switch between the upstream sample receiving line and the downstream sample receiving line such that the particle counter inlet can be operably connected to the upstream sample receiving line or the downstream sample receiving line, and wherein the downstream sample receiving line includes a downstream sample line restrictor valve for balancing the flow rate through the downstream rotameter with the flow rate through the upstream rotameter; and
wherein each of the upstream and downstream rotameter flow ratings are between 5% and 60% above the sample flow rating of the particle collector.

16. The sampling and counting system according to claim 15, wherein each of the upstream and downstream rotameter flow ratings are between 15% and 30% above the sample flow rating of the particle collector.

* * * * *